United States Patent
Mena

(10) Patent No.: US 6,302,693 B1
(45) Date of Patent: Oct. 16, 2001

(54) ENGAGEMENT MECHANISM FOR DENTAL PROSTHESES

(76) Inventor: Raul R. Mena, 201 N. University Dr. Suite 101, Plantation, FL (US) 33324

( * ) Notice: Subject to any disclaimer, the term of this patent is extended or adjusted under 35 U.S.C. 154(b) by 0 days.

(21) Appl. No.: 09/658,689

(22) Filed: Sep. 8, 2000

(51) Int. Cl.[7] .................................................. A61C 8/00
(52) U.S. Cl. .......................... 433/172; 433/169; 433/173
(58) Field of Search ................................. 433/169, 172, 433/173, 174, 175, 176

(56) References Cited

U.S. PATENT DOCUMENTS

| | | | |
|---|---|---|---|
| 4,568,285 | * | 2/1986 | Chiaramonte et al. ............. 433/169 |
| 5,071,350 | * | 12/1991 | Niznick ................. 433/173 |
| 5,098,295 | * | 3/1992 | Durr et al. ........................... 433/169 |

* cited by examiner

Primary Examiner—John J. Wilson
(74) Attorney, Agent, or Firm—J. Sanchelima

(57) ABSTRACT

An engagement mechanism for dental prostheses that include supporting pins with headed terminations and implant and/or abutment members with cooperative sockets. A dental implant firmly mounted to a user's bone is provided at the distal end with a socket defining a cavity of cooperative dimensions to receive the headed termination. The headed termination is firmly kept in the cavity. In this manner, better utilization of the limited inter dental space is achieved. One way of securing the headed termination is by using a cementitious compound to bind the headed termination. Another way is to use an O-ring to secure the headed termination. The socket can be positioned directly in the distal end of an implant member or in an abutment.

4 Claims, 2 Drawing Sheets

Fig. 4 — PRIOR ART

ENGAGEMENT MECHANISM FOR DENTAL PROSTHESES

BACKGROUND OF THE INVENTION

1. Field of the Invention

The present invention relates to a mechanism for engaging dental prostheses, and more particularly, to the type that includes an O-ring member.

2. Description of the Related Art

Many designs for engagement mechanisms have been designed in the past to support dental prostheses. All of them, however, include a socket in the prostheses thereby decreasing the available space and increasing the separation of engagement from the bone. By placing the socket in the abutment or a unitary implant post, the prosthesis is brought closer to the bone. This also lowers the stress point. The result is a better mechanism for supporting dental prostheses.

SUMMARY OF THE INVENTION

It is one of the main objects of the present invention to provide an abutment that increases the space available for the prosthesis by bringing the engagement close to the bone and surrounding tissue.

It is another object of this invention to provide an abutment that results in a more aesthetically appealing prosthesis.

It is still another object of the present invention to provide a lower fulcrum point resulting in less stress to the implant and surrounding bone and tissue.

It is yet another object of this invention to provide a lower stress point while increasing the space between teeth.

It is yet another object of this invention to provide a volumetrically efficient abutment that can be designed with different angles.

It is yet another object of this invention to provide an abutment that minimizes interference with the prosthesis by utilizing minimum engagement space.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 4 illustrates an exploded view of the prior art wherein the post member is mounted on the implant which in turn is mounted to the jaw bone and the socket is defined inside the prosthesis reducing the jaw bone and the socket is defined inside the prosthesis reducing the space available to mount tooth T.

DETAILED DESCRIPTION OF THE PREFERRED EMBODIMENT

Figure 1:
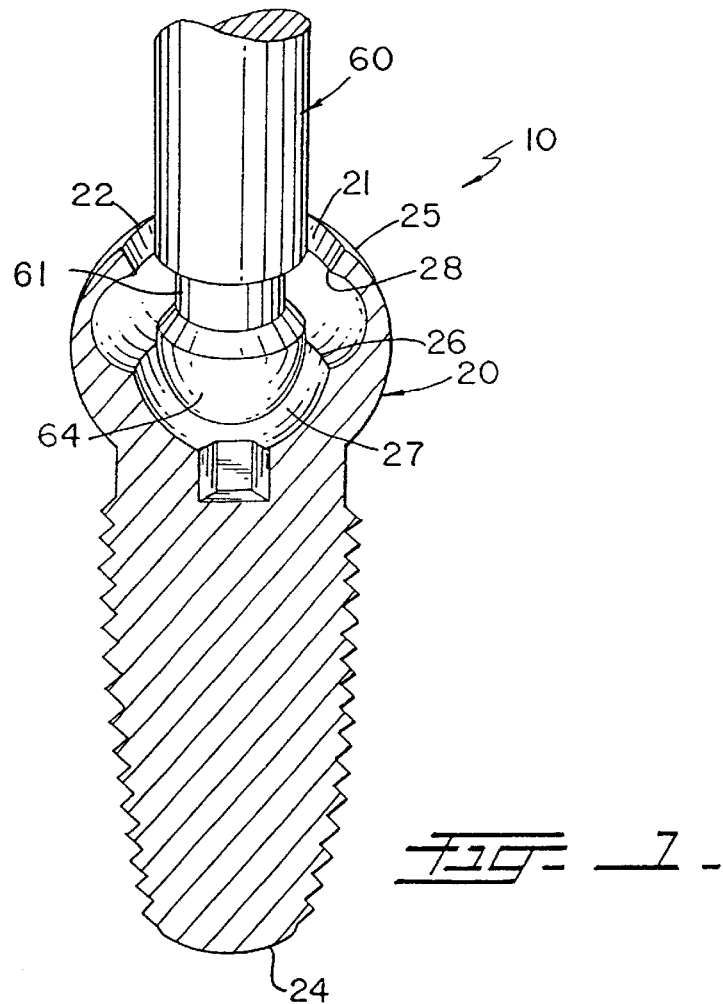
FIG. 1 is a partial cross-sectional view of a post member (attached to a prostheses) and implant member without the O-ring to appreciate the inner and outer ridges.

Referring now to the drawings, where the present invention is generally referred to with numeral 10, it can be observed that it basically includes dental implant member 20, O-ring 40, and post member 60 rigidly mounted to prosthesis P.

Figure 2:
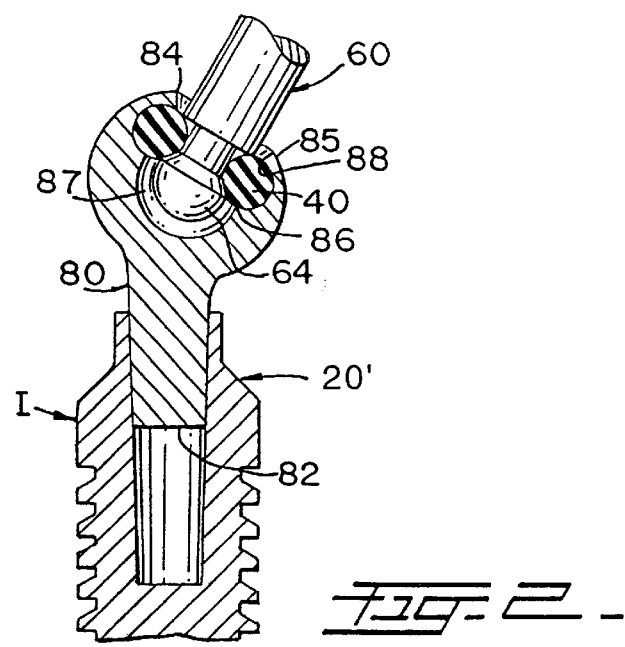
FIG. 2 represents a partial cross-sectional view of an alternate embodiment for the present invention, where the post is mounted at an angle with respect to the abutment.

Implant member 20 has two ends 22 and 24 and it is of the type that includes a built in abutment. End 24 is rigidly mounted to jaw bone B. End 22 includes socket 25 with an entrance 21. Inner and outer stopper ridges 26 and 28 are formed at a separate and spaced part relationship with respect to each other. Stopper ridges 26 and 28 are spaced apart a cooperative distance to snugly receive O-ring 40 in between and firmly hold it in place, as seen in FIG. 2. In FIG. 1 O-ring 40 has been omitted so that ridges 26 and 28 can be appreciated. Farther away from entrance 21, and adjacent to inner ridge 26, cavity 27 is defined for cooperatively lodging headed termination 64. Headed termination 64 is mounted to the end of shank 61 that has a smaller diameter.

O-ring 40 kept in place by inner stopper ridge 26 (or 86) and outer stopper ridge 28 (or 88). O-ring 40 is made of a special rubber. One suitable O-ring is manufactured by O-company, Inc. 600 Paisano N.E., Albuquerque, N. Mex. 87123 under part No. 4IOT1/T2/T3/T4/T5. This O-ring 40 permits headed termination 64 of post member 60 to be passed through lodging it within cavity 27 (or 87) when a predetermined force is applied to causing O-ring 40 to deform temporarily.

An alternate embodiment includes abutment 80 mounted to implant 20'. Abutment 80 includes socket 85 adjacent to end 84 and the other end 82 engages with an implant member 20'. Headed termination 64 is lodged within cavity 87, as shown in FIG. 2.

Figure 3:
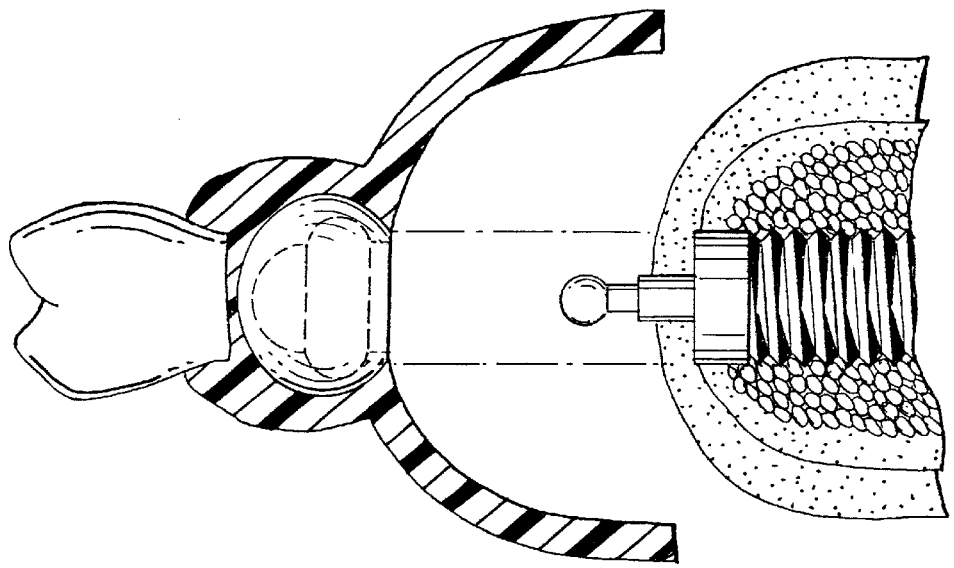
FIG. 3 illustrates an exploded view of one of the preferred embodiments for the present invention wherein the implant and the abutment are mounted to the jaw bone and the post is mounted to the prosthesis.
Figure 3:
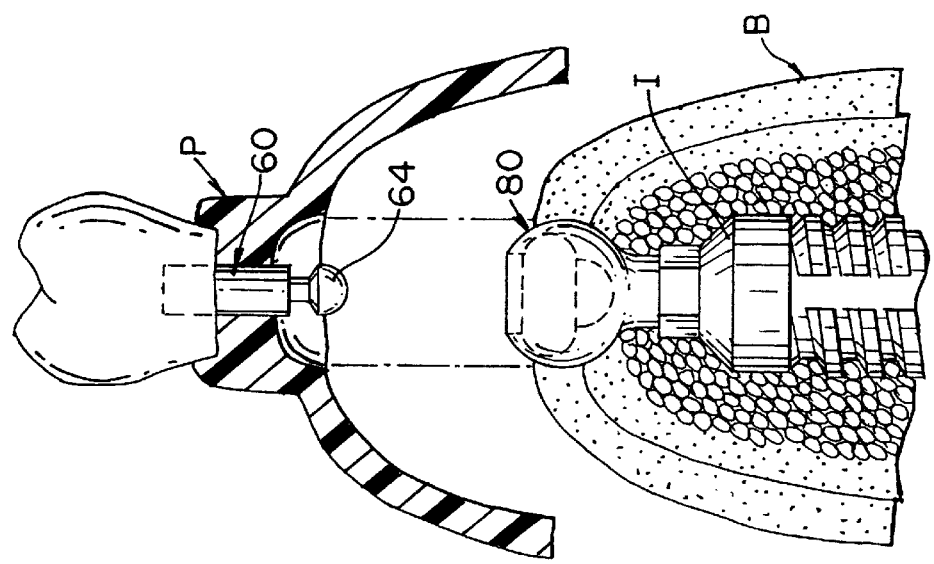

The important aspect of these embodiments is that the socket is not part of the prosthesis but rather is part of the abutment, or the implant (if the abutment is integral to the implant). This arrangement increases the available space in prosthesis P to mount teeth T or reduces the profile (height) of the prosthesis. This can be readily seen when the alternate embodiment represented in FIG. 3 is compared with the prior art represented in FIG. 4.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An engagement mechanism for a dental prosthesis, comprising:

A) dental implant means having first and second ends, said first end being mounted to a user's bone and said second end having a first socket defining a cavity and an entrance and further including internal outer and inner stopper ridges mounted at a parallel and spaced apart relationship with respect to each other;

B) an O-ring member cooperatively and snugly receivable within said outer and inner stopper ridges; and C) a post member having third and fourth ends, said third end being rigidly mounted to a prosthesis and said fourth end having a shank and a cooperative headed termination with a diameter larger than said shank and said headed termination being receivable within said cavity upon the application of a force of a predetermined magnitude to cause said headed termination to deform said O-ring member in passing there through said O-ring member being the sole support for said headed termination and shank and said second socket being cooperatively larger than said headed termination thereby securely lodging said headed termination in said cavity and said shank being surrounded by said O-ring member so that contact between said post member and said dental implant means is prevented.

2. The mechanism set forth in claim 1 wherein the length of said shank is substantially the same as the separation of said inner and outer stopper ridges.

3. An engagement mechanism for dental prostheses, comprising:

A) dental implant means having first and second ends, said first end being mounted to a user's bone and said second end includes a first socket and an entrance;

B) an abutment having third and fourth ends, said third end being mounted to said first socket in said second end and said fourth end having a second socket defining a cavity and further including internal outer and inner stopper ridges disposed at a parallel and spaced apart relationship with respect to each other; and C) an O-ring member cooperatively and snugly receivable within said outer and inner stopper ridges;

D) a post member having third and fourth ends, said third end being rigidly mounted to a prosthesis and said fourth end having a cooperative headed termination receivable within said cavity upon the application of a force of predetermined magnitude to cause said headed termination to deform said O-ring member in passing therethrough, said O-ring member being the sole support for said headed termination and shank and said second socket being cooperatively larger than said headed termination thereby lodging said headed termination between said cavity and said O-ring member so that contact between said post member and said abutment is prevented.

4. The mechanism set forth in claim 3 wherein the length of said shank is substantially the same as the separation of said inner and outer stopper ridges.

* * * * *